US006569872B1

(12) United States Patent
Leach et al.

(10) Patent No.: US 6,569,872 B1
(45) Date of Patent: May 27, 2003

(54) USE OF NEUROKININ RECEPTOR ANTAGONISTS TO TREAT ANDROGEN-DEPENDENT DISEASES

(75) Inventors: Michael W. Leach, Shrewsbury, MA (US); Mark R. Berardi, Sussex, NJ (US); Elmer J. Mirro, Wantage, NJ (US); Dineshwar Sinha, Newton, NJ (US); Jonathan A. Pachter, Maplewood, NJ (US); Mark E. Cartwright, Sparta, NJ (US); Gregory A. Reichard, Morris Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/140,843

(22) Filed: May 7, 2002

Related U.S. Application Data

(60) Provisional application No. 60/289,491, filed on May 8, 2001.

(51) Int. Cl.⁷ ................ A61K 31/445; A61K 31/50
(52) U.S. Cl. ................ 514/316; 514/254; 514/329
(58) Field of Search ................ 514/316, 254, 514/327

(56) References Cited

U.S. PATENT DOCUMENTS

| 5,350,852 A | 9/1994 | Emonds-Alt et al. |
| 5,432,175 A | 7/1995 | Piwinski et al. |
| 5,620,989 A | 4/1997 | Harrison et al. |
| 5,654,316 A | 8/1997 | Carruthers et al. |
| 5,665,735 A | 9/1997 | Friary et al. |
| 5,688,960 A | 11/1997 | Shankar |
| 5,691,362 A | 11/1997 | McCormick et al. |
| 5,696,267 A | 12/1997 | Reichard et al. |
| 5,719,156 A | 2/1998 | Shue et al. |
| 5,760,018 A | 6/1998 | Baker et al. |
| 5,783,579 A | 7/1998 | McCormick |
| 5,789,422 A | 8/1998 | Reichard et al. |
| 5,840,725 A | 11/1998 | Reichard et al. |
| 5,945,428 A | 8/1999 | Shih et al. |
| 5,968,929 A | 10/1999 | Blythin et al. |
| 6,063,926 A | 5/2000 | Reichard et al. |
| 6,204,265 B1 | 3/2001 | Reichard et al. |

FOREIGN PATENT DOCUMENTS

| WO | WO896/01105 | 2/1986 |
| WO | WO90/10462 | 9/1990 |
| WO | WO91/00731 | 1/1991 |
| WO | WO91/00733 | 1/1991 |
| WO | WO94/10165 | 5/1994 |
| WO | WO94/13639 | 6/1994 |
| WO | WO94/26767 | 11/1994 |
| WO | WO94/29309 | 12/1994 |
| WO | WO95/19344 | 7/1995 |
| WO | WO96/26201 | 8/1996 |
| WO | WO97/11162 | 3/1997 |
| WO | WO00/43008 | 7/2000 |

OTHER PUBLICATIONS

Debeljuk, L., Lasaga, M., *Modulation of the hypothalamo–pituitary–gonadal axis and the pineal gland by neurokinin A, neuropeptide K and neuropeptide γ*, Peptides 20 (1999), 285–299.

*Primary Examiner*—James H Reamer
(74) *Attorney, Agent, or Firm*—Allen N. Kutzenco; Palaiyur S. Kalyanaraman

(57) ABSTRACT

Use of an antagonist selected from the group consisting of: (a) antagonists of neurokinin-1 ($NK_1$), neurokinin-2 ($NK_2$) and neurokinin-3 ($NK_3$) receptors, (b) antagonists of $NK_1$ and $NK_2$ receptors, (c) antagonists of $NK_2$ and $NK_3$ receptors, (d) antagonists of $NK_1$ and $NK_3$ receptors, (e) antagonists of $NK_1$ receptors, and (f) antagonists of $NK_2$ to treat symptoms and disorders associated with a production and/or secretion of androgen. One aspect of the invention relates to the use of antagonists to suppress production/secretion of androgens in mammals suffering from an androgen-dependent disease, such as benign prostatic hyperplasia and prostatic carcinoma.

30 Claims, No Drawings

US 6,569,872 B1

USE OF NEUROKININ RECEPTOR ANTAGONISTS TO TREAT ANDROGEN-DEPENDENT DISEASES

RELATED APPLICATION

The application claims priority to U.S. Provisional Application 60/289,491, filed May 8, 2001.

FIELD OF THE INVENTION

The invention is directed to a method of treating an androgen-dependent disease in mammals, e.g., humans, with antagonists of neurokinin-1 ($NK_1$), neurokinin-2 ($NK_2$) and/or neurokinin-3 ($NK_3$) receptors. The invention further relates to the use of these antagonists for purposes of prophylactic modulation.

BACKGROUND OF THE INVENTION

An androgen-dependent disease is one which is exacerbated by, or caused by, excessive, inappropriate or unregulated androgen production. Examples of such diseases in men include, but are not limited to, benign prostatic hyperplasia (BPH), metastatic prostatic carcinoma, testicular cancer, androgen dependent acne, male pattern baldness and precocious puberty in boys. Examples of such diseases in women include, but are not limited to, hyperandrogenism, hirsutism, virilization, polycystic ovary syndrome (PCOS), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g., follicular maturation arrest, atresia, anovulation, dysmenorrhea, dysfunctional uterine bleeding, infertility) and androgen-producing tumors (virilizing ovarian or adrenal tumor).

Benign prostatic hyperplasia and prostatic carcinoma are among the most common afflictions of aging men.

Benign prostatic hyperplasia is often treated surgically with a procedure known as transurethral resection of the prostate (TURP). Other surgical procedures performed to release the obstruction of urine include incision or stents. Castration has also resulted in regression of prostatic enlargement. Drug therapy for BPH has included alpha-1 blockers which treat the symptoms of the disease by alleviating obstructive symptoms, but do not affect the underlying cause of the disease, the enlarged prostate gland. Representative alpha-1 blockers used in the treatment of BPH include: prazosin, terazosin, doxazosin, tamsulosin and alfuzosin. These drugs relax prostatic smooth muscle tone, decreasing intraurethral pressure without affecting bladder pressure. Common side effects of these agents are dizziness, headache and fatigue.

Both prostatic carcinoma and BPH have been treated with antiandrogens. A principal mediator of androgenic activity in the prostate is 5α-dihydrotestosterone (DHT), formed locally in the prostate by the action of testosterone-5α-reductase. Inhibitors of testosterone-5α-reductase inhibit the conversion of testosterone (T) to DHT and serve to prevent or lessen symptoms of hyperandrogenic stimulation in the prostate. Non-steroidal antiandrogens such as flutamide and Casodex compete with DHT for androgen receptor sites in the prostrate cells. These non-steroidal antiandrogens do not substantially change sexual potency and libido as the gonadotrophin releasing hormone agonists and progestogens do; however, these non-steroidal antiandrogens often exhibit the undesirable tendency to feminize the male host (gynaecomastia) or initiate feed-back effects which would cause hyperstimulation of the testes.

Luteinizing hormone (LH), under control of Gonadotropin Releasing Hormone (GnRH), is released by the pituitary gland and stimulates the production of androgens by the gonads. Androgens, the principle one being testosterone, are secreted mainly by the testes and, to a lesser degree, by the adrenal cortex and ovary. Suppression of gonadotropin production and/or secretion results in the suppression of androgen production and/or secretion.

Gonadotropin-releasing hormone (GnRH) agonists such as nafarelin, buserelin, goserelin and leuprorelin, reduce the release of luteinizing hormone (LH) by desensitizing the GnRH receptors in the anterior pituitary gland. GnRH agonists are able to reduce the production of testosterone, induce shrinkage of prostate volume and reduce the severity of urinary symptoms of BPH. Unfortunately, these drugs have adverse effects such as impotence and flushing, which discourage a majority of patients from continuing with the drugs. These androgen-suppressing agents are thus of inconsequential significance in BPH treatment, but are of major importance in the treatment of patients with advanced prostatic cancer. These initially can cause increased androgen production before desensitization occurs, which is a major side effect.

Progestogens, such as megestrol acetate, hydroxyprogesterone and medrogestone depress testosterone by inhibiting LH release and blocking androgen receptors, causing a reduction in prostatic volume. Adverse effects such as decreased libido and impotence have limited progestogens from common use in BPH treatment.

Thus, there remains a need for improved therapies for BPH and prostatic carcinoma, as well as other androgen-dependent diseases. There also remains a need for an additional method for the treatment of androgen-dependent diseases which utilizes non-steroidal compounds that possess different pharmacological properties from steroids.

Neurokinin receptors can be found in the nervous system, circulatory system and peripheral tissues of mammals. Consequently, the modulation of these types of receptors have been studied to potentially treat or prevent various mammalian disease states. Representative types of neurokinin receptor antagonists and the disorders that can be treated with them can be found in: U.S. Pat. No. 6,329,401 (2001) (sleep), U.S. Pat. No. 5,760,018 (1998) (pain, inflammation, migraine and emesis), U.S. Pat. No. 5,620,989 (1997) (pain, nociception and inflammation), WO 95/19344 (same), WO 94/13639 (same) and WO 94/10165 (same).

$NK_1$ and $NK_2$ receptor antagonists have also been disclosed in U.S. Pat. No. 5,350,852 and WO 94/29309.

WO 00/43008 discloses a method of suppressing gonadotropin and/or androgen production with specific $NK_3$ receptor antagonists.

SUMMARY OF THE INVENTION

One aspect of the invention provides a method of decreasing in vivo concentrations of androgens to normal or subnormal levels in a patient suffering from a disease state which is exacerbated by, or caused by excessive, inappropriate or unregulated androgen production or secretion. Another aspect of the invention provides a method of prophylactic androgen modulation.

Another aspect of the invention provides a method of treating a symptom or disorder associated with a production and/or secretion of androgen comprising administering to a patient in need of such treatment a therapeutically effective amount of an antagonist selected from the group consisting of: (a) antagonists of neurokinin-1 ($NK_1$), neurokinin-2 ($NK_2$) and neurokinin-3 ($NK_3$) receptors, (b) antagonists of $NK_1$ and $NK_2$ receptors, (c) antagonists of $NK_2$ and $NK_3$ receptors, (d) antagonists of $NK_1$ and $NK_3$ receptors, (e) antagonists of $NK_1$ receptors, and (f) antagonists of $NK_2$ receptors.

Further provided is a method of treating a symptom or disorder associated with a production and/or secretion of androgen, comprising administering to a patient in need of such treatment a therapeutically effective amount of a pharmaceutical composition comprising a pharmaceutically acceptable carrier and an antagonist selected from the group consisting of: (a) antagonists of neurokinin-1 ($NK_1$), neurokinin-2 ($NK_2$) and neurokinin-3 ($NK_3$) receptors, (b) antagonists of $NK_1$ and $NK_2$ receptors, (c) antagonists of $NK_2$ and $NK_3$ receptors, (d) antagonists of $NK_1$ and $NK_3$ receptors, (e) antagonists of $NK_1$ receptors, and (f) antagonists of $NK_2$ receptors.

Another aspect of the invention is directed to a method of treating a symptom or disorder associated with the production and/or secretion of androgen comprising administering to a patient in need of such treatment a therapeutically effective amount of a pharmaceutical composition comprising the antagonist of formula 1 shown below and a pharmaceutically acceptable carrier.

The invention also provides a method of treating a symptom or disorder associated with a production and/or secretion of androgen comprising administering to a patient in need of such treatment a therapeutically effective amount of a pharmaceutical composition comprising a pharmaceutically acceptable carrier and an antagonist selected from the group of compounds consisting of:

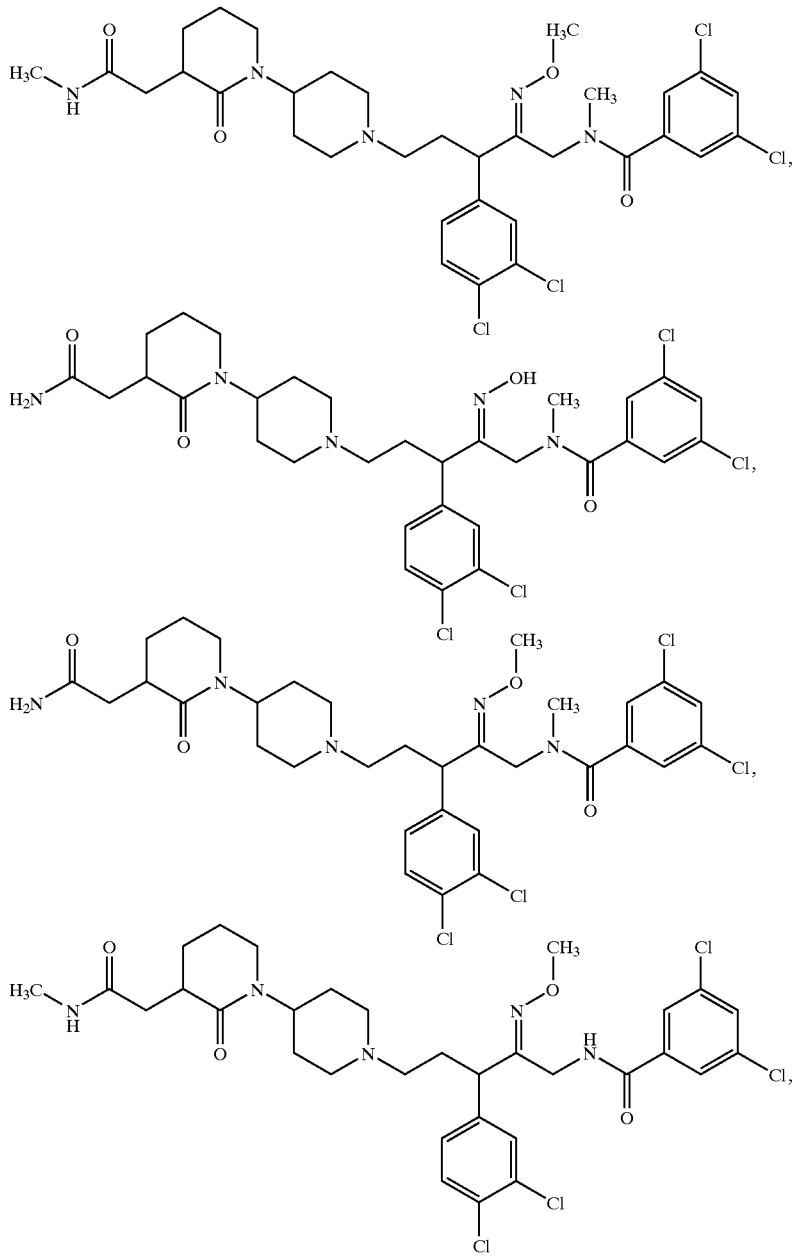

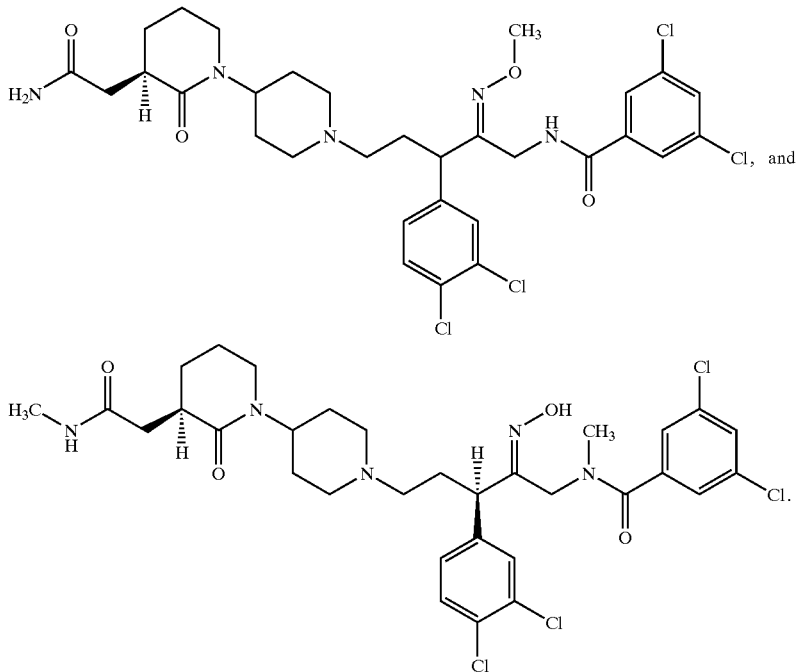

The invention further provides a method of treating a symptom or disorder associated with a production and/or secretion of luteinizing hormone (LH), comprising administering to a patient in need of such treatment a therapeutically effective amount of an antagonist selected from the group consisting of: (a) antagonists of neurokinin-1 ($NK_1$), neurokinin-2 ($NK_2$) and neurokinin-3 ($NK_3$) receptors, (b) antagonists of $NK_1$ and $NK_2$ receptors, (c) antagonists of $NK_2$ and $NK_3$ receptors, (d) antagonists of $NK_1$ and $NK_3$ receptors, (e) antagonists of $NK_1$ receptors, and (f) antagonists of $NK_2$ receptors.

The invention further provides a method of treating a symptom or disorder selected from the following: benign prostatic hyperplasia, metastatic carcinoma, testicular cancer, androgen dependent acne, male pattern baldness, precocious puberty in boys, hyperandrogenism, hirsutism, virilization, PCOS, HAIR-AN syndrome, ovarian hyperthecosis, follicular maturation arrest, atresia, anovulation, dysmenorrhea, dysfunctional uterine bleeding, infertility, and androgen-producing tumors, by modulating a production and/or secretion of androgen and/or luteinizing hormone, comprising administering to a patient in need of such treatment a therapeutically effective amount of an antagonist selected from the group consisting of: (a) antagonists of neurokinin-1 ($NK_1$), neurokinin-2 ($NK_2$) and neurokinin-3 ($NK_3$) receptors, (b) antagonists of $NK_1$ and $NK_2$ receptors, (c) antagonists of $NK_2$ and $NK_3$ receptors, (d) antagonists of $NK_1$ and $NK_3$ receptors, (e) antagonists of $NK_1$ receptors, and (f) antagonists of $NK_2$ receptors.

Also provided by the invention is a method of inhibiting a production and/or secretion of an androgen in a mammal comprising administering to the mammal an inhibitory amount of a compound according to formula 1 or formula 2 shown below.

The invention further provides a method of inhibiting a production and/or secretion of luteinizing hormone (LH) in a mammal comprising administering to the mammal an inhibitory amount of a compound according to formula 1 or formula 2 shown below.

Moreover, the invention provides a method of modulating a level of an androgen in a mammal comprising administering to the mammal an effective amount of a compound according to formula 1 or formula 2 shown below.

Further provided is a method of modulating a level of luteinizing hormone in a mammal comprising administering to the mammal an effective amount of a compound according to formula 1 or formula 2 shown below.

Representative (e.g., non-selective) antagonist compounds of neurokinin-1 ($NK_1$), neurokinin-2 ($NK_2$) and neurokinin-3 ($NK_3$) receptors which are useful in the methods of the invention are described and set forth in commonly assigned U.S. Pat. Nos. 5,696,267, 5,840,725 and 6,063,926, the entire contents of which are incorporated herein by reference.

Compounds useful in the methods of the invention, which are disclosed in U.S. Pat. No. 5,696,267 and in U.S. Pat. No. 5,840,725, are represented by the formula (1):

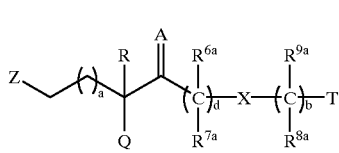

or a pharmaceutically acceptable salt thereof, wherein:

a is 0, 1, 2 or 3;

R is H, $C_{1-6}$ alkyl, —OH or $C_2$–$C_6$ hydroxyalkyl;

A is an optionally substituted oxime, optionally substituted hydrazone or optionally substituted olefin;

X is a bond, —C(O)—, —O—, —$NR^6$—, —S(O)$_e$—, —N($R^6$)C(O)—, —C(O)N($R^6$)— —OC(O)$NR^6$—, —OC(=S)$NR^6$—, —N($R^6$)C(=S)O—, —C(=$NOR^1$)—, —S(O)$_2$N($R^6$)—, —N($R^6$)S(O)$_2$—, —N($R^6$)C(O)O— or —OC(O)—;

b, d and e are independently 0, 1 or 2;

T is H, phthalimidyl, aryl, heterocycloalkyl, heteroaryl, cycloalkyl or bridged cycloalkyl;

Q is —SR$^6$, —N(R$^6$)(R$^7$), —OR$^6$, phenyl, naphthyl or heteroaryl;

R$^{6a}$, R$^{7a}$, and R$^{8a}$ are each independently H, C$_{1-6}$ alkyl, C$_2$-C$_6$ hydroxyalkyl, C$_1$-C$_6$ alkoxy-C$_1$-C$_6$ alkyl, phenyl or benzyl;

R$^6$ and R$^7$ are each independently H, C$_{1-6}$ alkyl, C$_2$-C$_6$ hydroxyalkyl, C$_1$-C$_6$ alkoxy-C$_1$-C$_6$ alkyl, phenyl or benzyl; or R$^6$ and R$^7$, together with the nitrogen to which they are attached, form a ring;

R$^{9a}$ is R$^6$ or —OR$^6$;

Z is morpholinyl, optionally N-substituted piperazinyl, optionally substituted

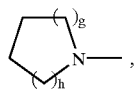

or substituted

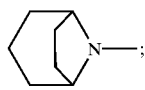

g is 0–3;

h is 1–4, provided the sum of h and g is 1–7;

wherein each aryl, heterocycloalkyl, heteroaryl, cycloalkyl and bridged cycloalkyl groups are all optionally substituted.

In particular, compounds useful in the methods of the invention, disclosed in U.S. Pat. No. 6,063,926, have the formula 2:

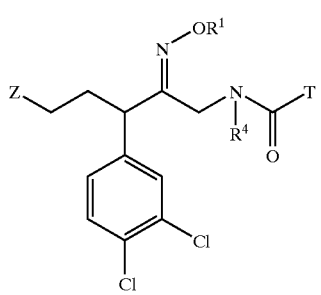

or a pharmaceutically acceptable salt thereof, wherein:

T is
1) phenyl, substituted with two or three substituents independently selected from the group consisting of:
   a) chloro;
   b) methyl, and
   c) methoxy; or
2) pyridyl, substituted with two or three substituents independently selected from the group consisting of:
   a) chloro, and
   b) methyl;

R$^1$ is H, methyl, ethyl, —CH$_2$CN, —CH$_2$C(O)NH$_2$, —(CH$_2$)$_3$SO$_3$H, —CH$_2$C(O)NHCH$_3$, —CH$_2$C(O)NHOH, —CH$_2$C(O)NHOCH$_3$, —CH$_2$C(O)NHCH$_2$CN, —CH$_2$F, —CH$_2$C(O)NHCH$_2$SO$_3$H,

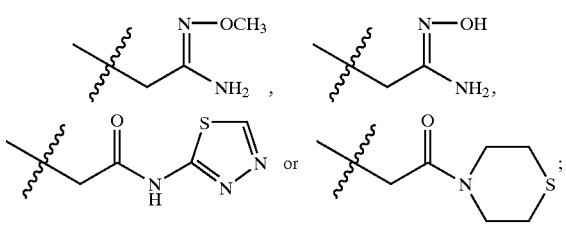

R$^4$ is methyl or ethyl; and

Z is

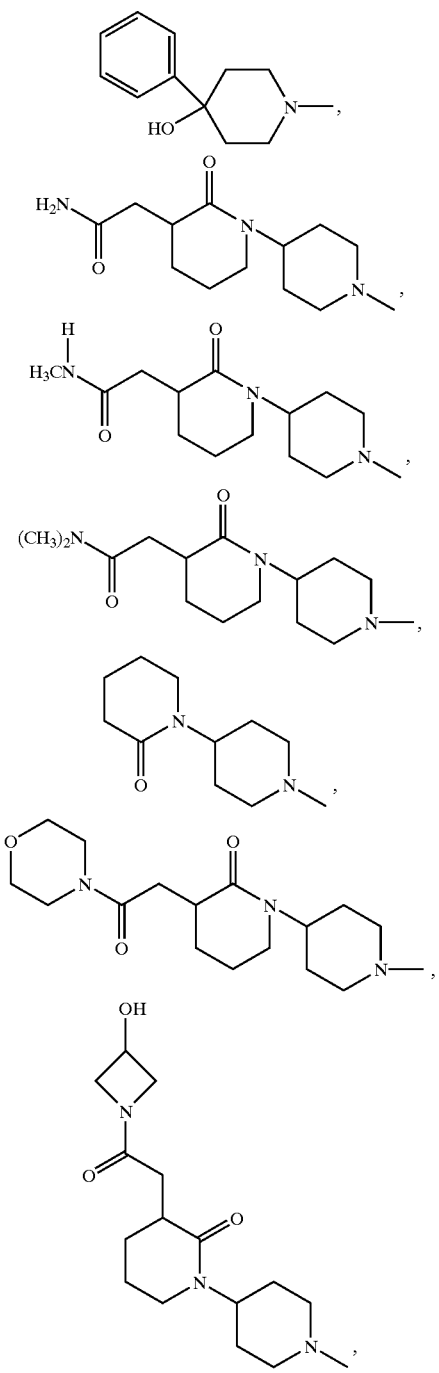

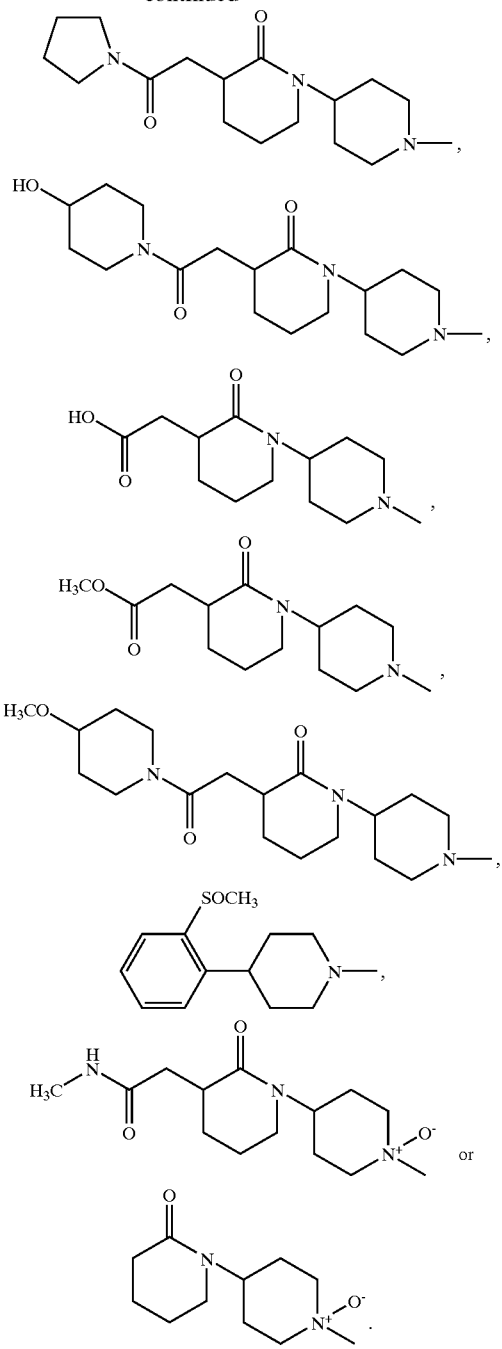

The invention further provides methods of treatment that employ compounds having formula 1 or formula 2, including any and all isomers, such as enantiomers, stereoisomers, diastereomers, rotomers, tautomers, etc., and prodrugs of the compounds having formula 1 or 2, and the isomers thereof, and their corresponding salts, solvates (e.g., hydrates), esters, and the like. The invention further encompasses methods of treatment that employ pharmaceutically-acceptable compositions prepared from one or more compounds according to formulae 1 and 2 and one or more pharmaceutically-acceptable excipients/carriers, or salts, solvates, esters, etc., thereof. The compounds having formulae 1 and 2 can be useful for treating androgen-dependent symptoms and disorders, such as diseases. Accordingly, the invention includes methods of treating a symptom or disorder associated with a production and/or secretion of androgen by administering to a patient in need of such treatment an effective amount of a pharmaceutical composition comprising at least one compound having formula 1 or formula 2 and at least one pharmaceutically-acceptable excipient/carrier.

Preferably, the invention relates to the use of one or more compounds of formula 1 or 2, or pharmaceutical salts thereof, in pharmaceutical compositions for the treatment of BPH, metastatic prostatic carcinoma, testicular cancer, androgen dependent acne, male pattern baldness, precocious puberty in boys, hyperandrogenism, hirsutism, virilization, PCOS, HAIR-AN syndrome, ovarian hyperthecosis, follicular maturation arrest, atresia, anovulation, dysmenorrhea, dysfunctional uterine bleeding, infertility, and androgen-producing tumors.

A further understanding of the invention will be had from the following detailed description of the invention, including its preferred embodiments.

DETAILED DESCRIPTION

Definitions and Usage of Terms

The following definitions and terms are used herein or are otherwise known to a skilled artisan. Except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

Unless otherwise known, stated or shown to be to the contrary, the point of attachment for a multiple term substituent (multiple terms that are combined to identify a single moiety) to a subject structure is through the last named term of the multiple term. For example, a cycloalkylalkyl substituent attaches to a targeted through the latter "alkyl" portion of the substituent (e.g., Structure-alkyl-cycloalkyl).

The identity of each variable appearing more than once in a formula may be independently selected from the definition for that variable, unless otherwise indicated.

Unless stated, shown or otherwise known to be the contrary, all atoms illustrated in chemical formulas for covalent compounds possess normal valencies. Thus, hydrogen atoms, double bonds, triple bonds and ring structures need not be expressly depicted in a general chemical formula.

Double bonds, where appropriate, may be represented by the presence of parentheses around an atom in a chemical formula. For example, a carbonyl functionality, —CO—, may also be represented in a chemical formula by —C(O)— or —C(=O)—. Similarly, a double bond between a sulfur atom and an oxygen atom may be represented in a chemical formula by —SO—, —S(O)— or —S(=O)—. One skilled in the art will be able to determine the presence or absence of double (and triple bonds) in a covalently-bonded molecule. For instance, it is readily recognized that a carboxyl functionality may be represented by —COOH, —C(O)OH, —C(=O)OH or —CO₂H.

The term "substituted," as used herein, means the replacement of one or more atoms or radicals, usually hydrogen atoms, in a given structure with an atom or radical selected from a specified group. In the situations where more than one atom or radical may be replaced with a substituent selected from the same specified group, the substituents may be, unless otherwise specified, either the same or different at every position. Radicals of specified groups, such as alkyl, cycloalkyl, heterocycloalkyl, aryl and heteroaryl groups, independently of or together with one another, may be substituents on any of the specified groups, unless otherwise indicated. Unless noted otherwise, preferred substitution groups for formula 1 herein are the same as those disclosed in U.S. Pat. Nos. 5,840,725, 5,696,267; and preferred substitution groups for formula 2 herein are the same as those disclosed in U.S. Pat. No. 6,063,926.

The term "chemically-feasible" is usually applied to a ring structure present in a compound and means that the ring structure (e.g., a 4- to 7-membered ring, optionally substituted by . . . ) would be expected to be stable by a skilled artisan.

The term "heteroatom," as used herein, means a nitrogen, sulfur, or oxygen atom. Multiple heteroatoms in the same group may be the same or different.

The term "alkyl," as used herein, means an unsubstituted or substituted, straight or branched, hydrocarbon chain (i.e., comprising carbon and hydrogen atoms bonded together), having, preferably, from one to twenty-four carbon atoms, more preferably, from one to twelve carbon atoms, and even more preferably, from one to six carbon atoms.

The term "cycloalkyl" or "cycloalkane," as used herein, means an unsubstituted or substituted, saturated, stable, non-aromatic, chemically-feasible carbocyclic ring, having, preferably, from three to fifteen carbon atoms, more preferably, from three to eight carbon atoms. The cycloalkyl carbon ring radical is saturated and may be fused, for example, benzofused, with one to two cycloalkyl, aromatic, heterocyclic or heteroaromatic rings. The cycloalkyl may be attached at any endocyclic carbon atom that results in a stable structure. Preferred carbocyclic rings have from five to six carbons. Examples of cycloalkyl radicals include cyclopropyl, cyclobutyl, cyclopentyl, cyclohexyl, cycloheptyl, and the like.

The term "aryl," as used herein, means a substituted or unsubstituted, aromatic, mono- or bicyclic, chemically-feasible carbocyclic ring system having from one to two aromatic rings. The aryl moiety will generally have from 6 to 14 carbon atoms with all available substitutable carbon atoms of the aryl moiety being intended as possible points of attachment. Representative examples include phenyl, tolyl, xylyl, cumenyl, naphthyl, tetrahydronaphthyl, indanyl, indenyl and the like. If desired, the carbocyclic moiety can be substituted with from one to five, preferably, one to three, moieties, such as mono-through pentahalo, alkyl, trifluoromethyl, phenyl, hydroxy, alkoxy, phenoxy, amino, monoalkylamino, dialkylamino, and the like.

The term "heteroaryl," as used herein, means a mono- or bicyclic, chemically-feasible ring system containing one or two aromatic rings and at least one nitrogen, oxygen or sulfur atom in the aromatic ring. Mono- and polycyclic (e.g., bicyclic) heteroaryl groups can be unsubstituted or substituted with a plurality of substituents, preferably, one to five substituents, more preferably, one, two or three substituents (e.g., mono-through pentahalo, alkyl, trifluoromethyl, phenyl, hydroxy, alkoxy, phenoxy, amino, monoalkylamino, dialkylamino, and the like). Typically, a heteroaryl group represents a chemically-feasible cyclic group of five or six atoms, or a chemically-feasible bicyclic group of nine or ten atoms, at least one of which is carbon, and having at least one oxygen, sulfur or nitrogen atom interrupting a carbocyclic ring having a sufficient number of pi ($\pi$) electrons to provide aromatic character. Representative heteroaryl (heteroaromatic) groups are pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, isothiazolyl, benzothiazolyl, benzoxazolyl, oxazolyl, pyrrolyl, isoxazolyl, 1,3,5-triazinyl and indolyl groups.

The term "heterocycloalkyl," as used herein, means an unsubstituted or substituted, saturated, chemically-feasible cyclic ring system having from three to fifteen members, preferably, from three to eight members, and comprising carbon atoms and at least one heteroatom as part of the ring.

The term "heterocyclic ring" or "heterocycle," as used herein, means an unsubstituted or substituted, saturated, unsaturated or aromatic, chemically-feasible ring, comprised of carbon atoms and one or more heteroatoms in the ring. Heterocyclic rings may be monocyclic or polycyclic. Monocyclic rings preferably contain from three to eight atoms in the ring structure, most preferably, five to seven atoms. Polycyclic ring systems consisting of two rings preferably contain from six to sixteen atoms, most preferably, ten to twelve atoms. Polycyclic ring systems consisting of three rings contain, preferably, from thirteen to seventeen atoms, most preferably, fourteen to fifteen atoms. Each heterocyclic ring has at least one heteroatom. Unless otherwise stated, the heteroatoms may each be independently selected from the group consisting of the following: nitrogen, sulfur and oxygen atoms.

The term "carbocyclic ring" or "carbocycle," as used herein, means an unsubstituted or substituted, saturated, unsaturated or aromatic (e.g., aryl), chemically-feasible hydrocarbon ring, unless otherwise specifically identified. Carbocycles may be monocyclic or polycyclic. Monocyclic rings, preferably, contain from three to eight atoms, more preferably, five to seven atoms. Polycyclic rings having two rings, preferably, contain from six to sixteen atoms, more preferably, ten to twelve atoms, and those having three rings, preferably, contain from thirteen to seventeen atoms, more preferably, fourteen to fifteen atoms.

The term "alkoxy," as used herein, means an oxygen atom bonded to a hydrocarbon chain, such as an alkyl group (—O-alkyl). Representative alkoxy groups include methoxy, ethoxy and isopropoxy groups.

The term "hydroxyalkyl," as used herein, means a substituted hydrocarbon chain, preferably, an alkyl group, having at least one hydroxy substituent (—alkyl—OH). Additional substituents to the alkyl group may also be present. Representative hydroxyalkyl groups include hydroxymethyl, hydroxyethyl and hydroxypropyl groups.

The term "halo," "halogen" or "halide," as used herein, means a chloro, bromo, fluoro or iodo atom radical. Chlorides, bromides and fluorides are preferred halides.

The term "sulfonyl," as used herein, represents a group having the formula —S(O)$_2$—.

The term "prodrug," as used herein, represents compounds that are drug precursors which, following administration to a patient, release the drug in vivo via a chemical or physiological process (e.g., a prodrug on being brought to a physiological pH or through an enzyme action is converted to the desired drug form). A discussion of prodrugs is provided in T. Higuchi and V. Stella, Pro-drugs as *Novel Delivery Systems*, Vol. 14 of A.C.S. Symposium Series (1987), and in *Bioreversible Carriers in Drug Design*, E. B. Roche, ed., American Pharmaceutical Ass'n and Pergamon Press (1987), each of which is incorporated herein by reference in its entirety.

The terms "compound having the formula 1", "compound having the formula 2", and the like as used herein, represent a compound having a chemical structure encompassed by formula 1 or formula 2, and includes any and all isomers (e.g., enantiomers, stereoisomers, diastereomers, rotomers, tautomers) and prodrugs of the compound. These compounds can be neutral, acidic or alkaline, and further include their corresponding pharmaceutically-acceptable salts, solvates, esters, and the like.

The phrase "effective amount," as used herein, means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

By the term "disorder", it is meant an abnormal physical or mental condition. As used herein, "disorders" include, but are not limited to, diseases.

By the term "symptom", it is meant subject evidence of disease or something that indicates the presence of a bodily disorder, such as, but not limited to, a disease.

The phrase "inhibitory amount", as used herein, means an amount of a compound or composition which is sufficient to reduce the level or activity of a biological agent to a value less as compared to when the compound or composition is not present.

In a preferred embodiment of the compounds of the formula 1 or 2,

T is phenyl, substituted with two or three substituents independently selected from the group consisting of:
  a) chloro;
  b) methyl, and
  c) methoxy.

More preferably, T is phenyl, substituted with
  a) two chloro substituents, or
  b) two methyl substituents (preferably 3,5-dichloro or 3,5-dimethyl), or
  c) two methoxy and one methyl substituent (i.e., 3,5-methoxy-4-methyl), with two chloro substituents being most preferred.

Also preferred are compounds of the formulas 1 or 2 wherein $R^1$ is methyl, —CH$_2$F, —CH$_2$CN, —(CH$_2$)$_3$SO$_3$H,

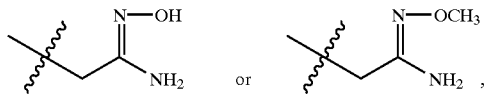

with methyl being more preferred.

$R^4$ is preferably methyl.

Another group of preferred compounds are those wherein Z is

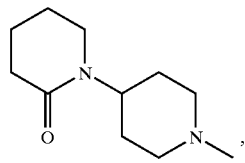

-continued

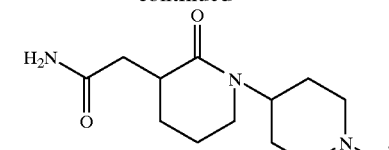

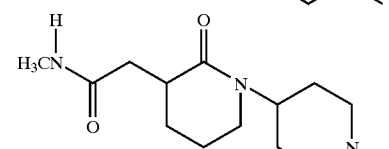

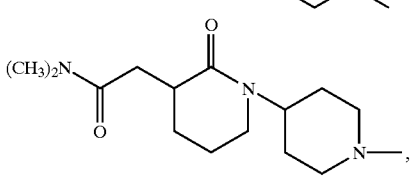

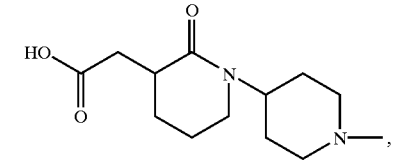

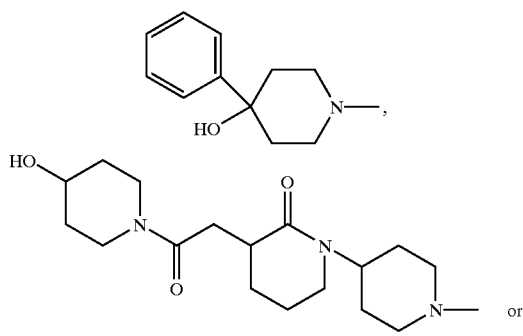 or

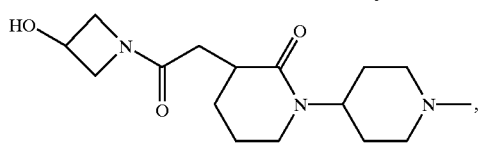

with

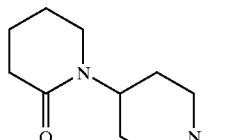

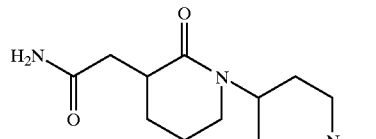

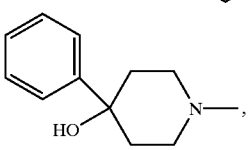

-continued

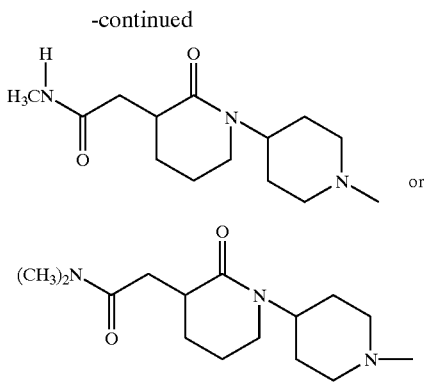

being more preferred, and

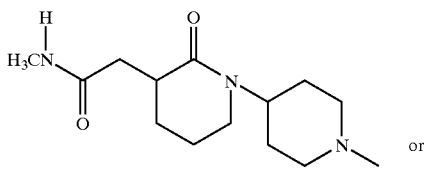

or

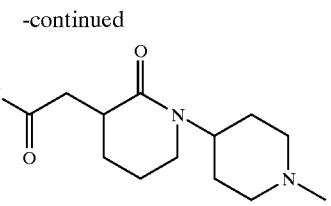

being most preferred.

In one aspect of the invention, compounds suitable for use in the methods of the invention are non-selective NK receptor antagonists. For example, useful non-selective NK antagonists are disclosed in the following U.S. Pat. Nos.: 5,688,960, 5,696,267, 5,840,725, 5,945,428, 6,063,926, and 6,204,265, each of which is incorporated herein in its entirety by reference.

The following compounds are preferred for use in accordance with the method of the invention:

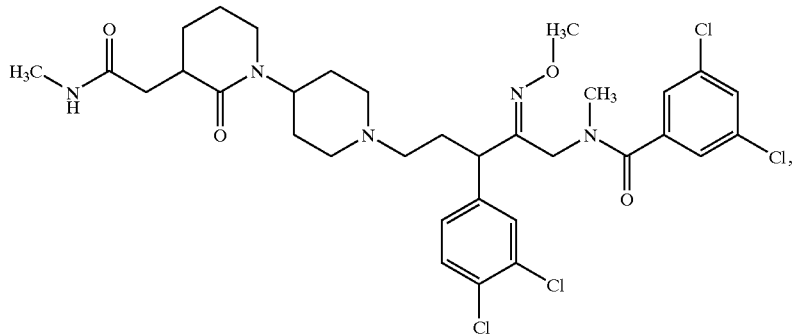

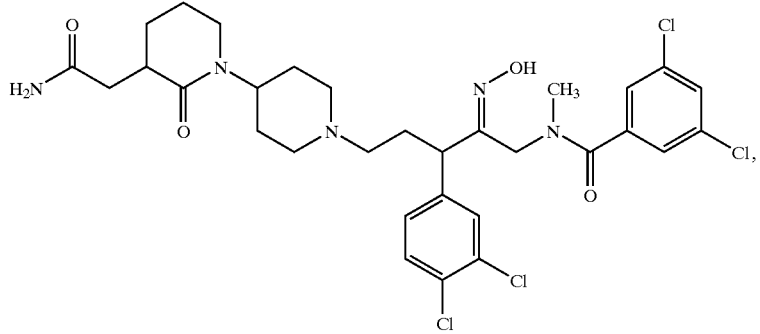

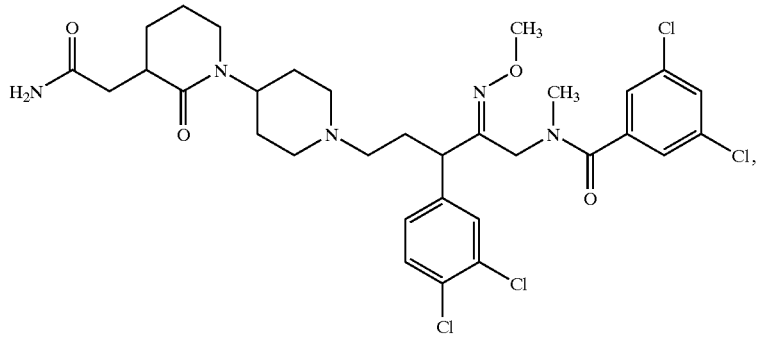

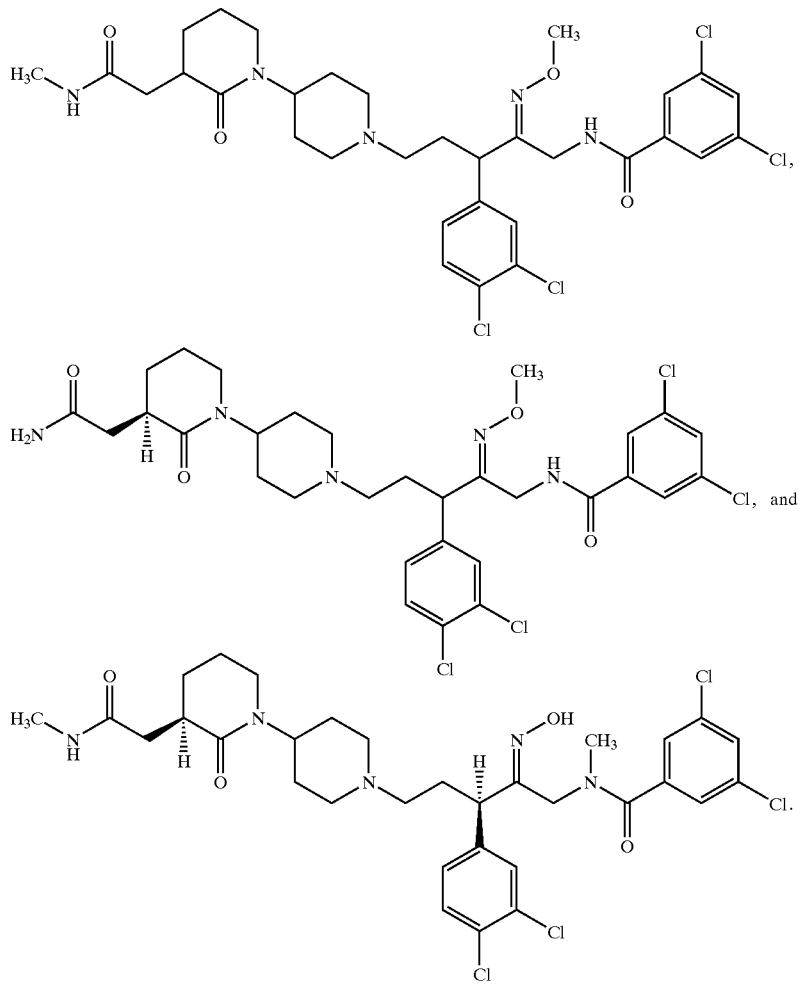

Compounds useful in the methods of the invention and methods for their syntheses are described in the aforementioned U.S. Pat. Nos. 5,696,267, 5,840,725 and 6,063,926, which are incorporated herein in their entirety by reference.

Compounds suitable for the methods of the present invention can have at least one asymmetric carbon atom and all isomers, including diastereomers, enantiomers and rotational isomers, as well as E and Z isomers of the oxime, hydrazone and olefin groups, are contemplated. The compounds include d and l isomers, in both pure form and in admixture, including racemic mixtures. Isomers can be prepared using conventional techniques, either by reacting optically pure or optically enriched starting materials or by separating isomers of a compound. The Z-isomers of the compounds of formulas 1 or 2 are preferred.

Those skilled in the art will appreciate that, for some compounds useful for practice of the present invention, one isomer will show greater pharmacological activity than other isomers.

Compounds for use in the methods of the invention have at least one amino group which can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, tartaric, methanesulfonic and other mineral and carboxylic acids well known to those in the art.

The salt is prepared by contacting the free base form with a sufficient amount of the desired acid to produce a salt. The free base form may be regenerated by treating the salt with a suitable dilute aqueous base solution such as dilute aqueous sodium bicarbonate.

Certain compounds suitable for use in the present invention are acidic (e.g., those compounds which posses a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

The compounds for use in the inventive methods can exist in unsolvated as well as solvated forms, including hydrated forms. In general, the solvated forms, with pharmaceutically-acceptable solvents, such as water, ethanol, and the like, are equivalent to the unsolvated forms for purposes of this invention.

Disorders or symptoms which may be treated with an antagonist of one or more of the $NK_1$, $NK_2$, and $NK_3$ receptors in accordance with this invention include, but are not limited to, BPH, metastatic prostatic carcinoma, testicular cancer, androgen dependent acne, male pattern baldness, precocious puberty in boys, hyperandrogenism, hirsutism, virilization, PCOS, HAIR-AN syndrome, ovarian hyperthecosis, follicular maturation arrest, atresia, anovulation, dysmenorrhea, dysfunctional uterine bleeding, infertility, and androgen-producing tumors.

A pharmaceutical composition comprising the antagonist of the $NK_1$, $NK_2$ and/or $NK_3$ receptors for use in the inventive methods may be prepared by admixture of a compound exhibiting such activity, and preferably, one or more compounds specifically described herein, with an appropriate carrier which may contain a diluent, binder, filler, disintegrant, flavoring agent, coloring agent, lubricant or preservative in conventional manner. A pharmaceutical composition typically contains from about 0.1 to about 99.9 weight percent, preferably, from about 5 to about 95 weight percent, more preferably, from about 20 to about 80 weight percent, of active ingredient (i.e., non-selective antagonist of the $NK_1$, $NK_2$, and/or $NK_3$ receptors).

Preferably, the pharmaceutical composition is in unit dosage form and in a form adapted for use in the medical or veterinarial fields. For example, such preparations may be in a pack form accompanied by written or printed instructions for use as an agent in the treatment of the conditions.

The suitable dosage range for the compounds of the invention depends on the compound to be employed and on the condition of the patient. It will also depend, inter alia, upon the relation of potency to absorbability and the frequency and route of administration.

The quantity of active ingredient (i.e., non-selective antagonist of the $NK_1$, $NK_2$ and/or $NK_3$ receptors) in a unit dose of preparation may be varied or adjusted from about 0.01 to about 4,000 mg, preferably, from about 0.02 to about 1,000 mg, more preferably, from about 0.3 to about 500 mg, and most preferably, from about 0.04 to about 250 mg, according to the particular application. A typical recommended daily dosage regimen for oral administration can range from about 0.02 to about 2,000 mg/day, in two to four divided doses. For convenience, the total daily dosage may be divided and administered in portions during the day as required. Typically, pharmaceutical compositions of the invention will be administered from about 1 to about 5 times per day, or alternatively, as a continuous infusion. Such administration can be used as a chronic or acute therapy. The amount of active ingredient that may be combined with carrier materials to produce a single dosage form will vary depending upon the host treated and the particular mode of administration.

The pharmaceutical composition may be formulated for administration by any route, and is preferably in unit dosage form or in a form that a human patient may self-administer in a single dosage. Advantageously, the composition is suitable for oral, rectal, topical, parenteral, intravenous or intramuscular administration. Preparations may be designed to give slow release of the active ingredient.

Pharmaceutical compositions may, for example, be in the form of tablets, capsules, sachets, vials, powders, granules, lozenges, reconstitutable powders, or liquid preparations, for example solutions or suspensions, or suppositories.

The pharmaceutical compositions, for example those suitable for oral administration, may contain conventional excipients such as binding agents, such as syrup, acacia, gelatin, sorbitol, tragacanth, or polyvinylpyrrolidone; fillers, such as lactose, sugar, maize-starch, calcium phosphate, sorbitol or glycine; tabletting lubricants, such as, magnesium stearate; disintegrants, such as starch, polyvinylpyrrolidone, sodium starch glycollate or microcrystalline cellulose; or pharmaceutically acceptable setting agents such as sodium lauryl sulphate.

Solid pharmaceutical compositions may be obtained by conventional methods of blending, filling, tabletting or the like. Repeated blending operations may be used to distribute the active agent throughout those compositions employing large quantities of fillers. When the medicament is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The medicament may also be in the form of an ingestible capsule, such as of gelatin containing the compound, optionally with a carrier or other excipients.

Pharmaceutical compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminum stearate gel, hydrogenated edible fats; emulsifying agents, such as lecithin, sorbitan monooleate, or acacia; aqueous or non-aqueous vehicles which include edible oils, such as almond oil, fractionated coconut oil, oily esters, such as esters of glycerine, or propylene glycol, or ethyl alcohol, glycerine, water or normal saline; preservatives, such as methyl or propyl ph-hydroxybenzoate or sorbic acid; and if desired conventional flavoring or coloring agents.

The compounds disclosed herein may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g., sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit-dose form such as ampoules or disposable injection devices or in multi-dose forms such as a bottle from which the appropriate dose may be withdrawn or a solid form or concentrate which can be used to prepare an injectable formulation.

The compounds disclosed herein may also be administered by inhalation, via intranasal or oral routes. Such administration can be carried out with a spray formulation comprising a compound of the invention and a suitable carrier, optionally suspended in, for example, a hydrocarbon propellant.

Preferred spray formulations comprise micronized compound particles in combination with a surfactant, solvent or a dispersing agent to prevent the sedimentation of suspended particles. Preferably, the compound particle size is from about 2 to 10 microns.

A further mode of administration of the compounds described herein comprises transdermal delivery utilizing a skin-patch formulation. A preferred formulation comprises a compound of the invention dispersed in a pressure sensitive adhesive which adheres to the skin, thereby permitting the compound to diffuse from the adhesive through the skin for delivery to the patient. For a constant rate of percutaneous absorption, pressure sensitive adhesives known in the art such as natural rubber or silicone can be used.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the therapeutic agents will be regulated according to the judgment of the attending clinician (physician) considering such factors as age, condition and size of the patient as well as severity of the disease being treated.

Preferably, the pharmaceutical preparation is in unit dosage form. In such form, the preparation is subdivided into unit doses containing appropriate quantities of the active component, e.g., an effective amount to achieve the desired purpose.

A unit dose will generally contain from 20 to 1000 mg and preferably will contain from 30 to 500 mg, in particular 50, 100, 150, 200, 250, 300, 350, 400, 450, or 500 mg. The composition may be administered one or more times a day, and the total daily dose for a 70 kg adult will normally be in the range of 100 to 3000 mg. Alternatively the unit dose will contain from 2 to 20 mg of active ingredient and be administered in multiples, if desired, to give the preceding daily dose.

Neurokinin B has been shown to interact with the $NK_3$ receptor; however similar to substance P and neurokinin A, neurokinin B has overlapping specificity with other NK receptors. Furthermore, there have been recent disclosures of the involvement of neurokinin B, as well as possibly substance P and neurokinin A in the hypothalamic-pituitary axis (Debeljuk, L. and Lasaga, M. Peptides 1999, 20,285). As described above, the pituitary gland is involved in the stimulation of production of androgens by the gonads. Since any of these three neuropeptides is capable of eliciting responses from all three neurokinin receptors, it is likely that inhibition of two or more of the neurokinin receptors may lead to a greater reduction in androgen production relative to that obtained when only one of the NK receptors is inhibited.

Compounds having the formula 1 or 2 can be effective antagonists of at least one receptor selected from the group consisting of neurokinin-1 ($NK_1$), neurokinin-2 ($NK_2$) and neurokinin-3 ($NK_3$) receptors. In one aspect of the invention, $NK_1$ selective antagonists are utilized in the methods of the invention. In another aspect of the invention, $NK_2$ selective antagonists are utilized in the methods of the invention. In preferred embodiments of the methods of the invention, the compounds antagonize two or more of the $NK_1$, $NK_2$ and $NK_3$ receptors. In more preferred embodiments of the methods of the invention, the compounds non-selectively antagonize all three of the $NK_1$, $NK_2$ and $NK_3$ receptors The compounds of the inventive method can be used to affect androgen production in a mammal (e.g., humans, dogs, cats, etc.). They can be administered to cause a chemical castration in a mammal (both male and female). Thus, male dogs can be neutered and female cats can be spayed with the inventive method. The inventive method can also be used to treat patients desiring prophylactic androgen modulation.

The in vitro and in vivo $NK_1$, $NK_2$ and $NK_3$ activities of the compounds having formula 1 or 2 can be determined by various procedures known in the art, such as a test for their ability to inhibit the activity of the $NK_1$ agonist Substance P, an isolated hamster trachea $NK_2$ assay, measurement of $NK_2$ activity in vivo in guinea pigs, measurement of bronchoconstriction due to NKA and neurokinin receptor binding assay(s). Typical procedures are described in WO 96/34857. Procedures for determining $NK_3$ activity may be found in, for example, *Molecular Pharmacol.*, 48 (1995), p. 711–716.

The percent inhibition of neurokinin agonist activity is the difference between the percent of maximum specific binding ("MSB") and 100%. The percent of MSB is defined by the following equation, wherein "dpm" represents "disintegrations per minute":

$$\% \text{ MSB} = \frac{(\text{dpm of unknown}) - (\text{dpm of nonspecific binding})}{(\text{dpm of total binding}) - (\text{dpm of nonspecific binding})} \times 100$$

The concentration at which a compound having formula 1 or 2 produces 50% inhibition of binding is then used to determine an inhibition constant ("Ki") using the Chang-Prusoff equation.

It will be recognized that the compounds having formula 1 or 2 can exhibit $NK_1$, $NK_2$ and $NK_3$ receptor antagonist activities of varying degrees. For instance, certain compounds can exhibit strong $NK_1$ antagonist activity, but weaker $NK_2$ and $NK_3$ antagonist activity, while other compounds may be strong $NK_2$ antagonists, but weaker $NK_1$ and $NK_3$ antagonists.

The compounds useful for practice of the invention exhibit potent affinities for one or more of the $NK_1$, $NK_2$ and $NK_3$ receptors as measured by Ki values (in nM). The activities (potencies) for these compounds are determined by measuring their Ki values. The smaller the Ki value, the more active is a compound for antagonizing a particular NK receptor. Suitable compounds for use in the invention may exhibit a wide range of activities. The average Ki values for the $NK_1$, $NK_2$ and $NK_3$ receptors of compounds for use with the inventive methods generally range from >0 nM (e.g., 0.01 nM) to about 1000 nM, preferably, from about 0.05 nM to about 500 nM, with values of from about 0.1 nM to about 100 nM being more preferred.

BIOLOGICAL DATA

The androgen-suppressing effect of compounds which are antagonists of one or more of $NK_1$, $NK_2$, and $NK_3$ receptors have been determined as follows:

The compounds in Table I below were evaluated:

TABLE I

COMPOUND A

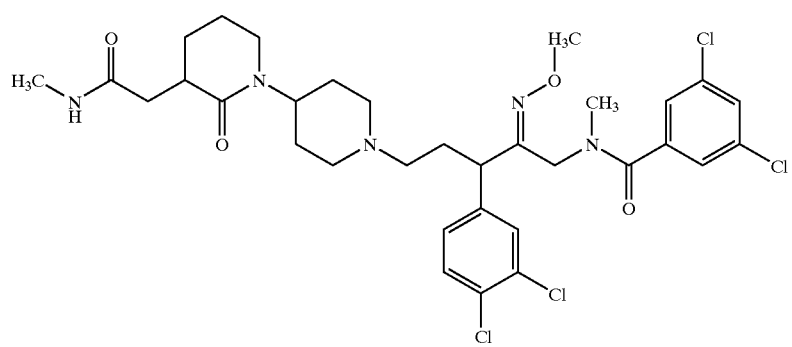

TABLE I-continued
COMPOUND B
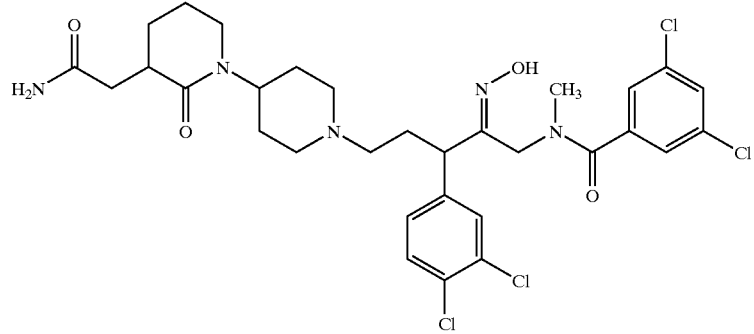
COMPOUND C
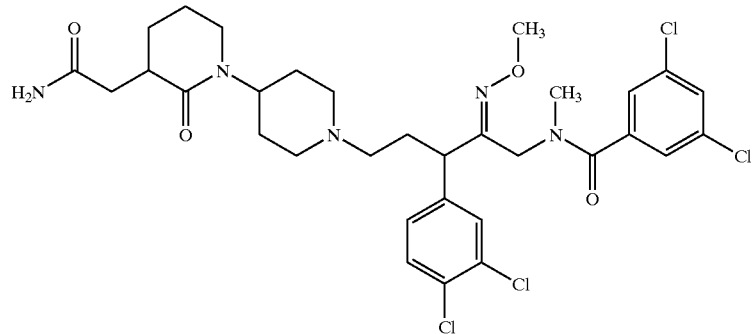
COMPOUND D
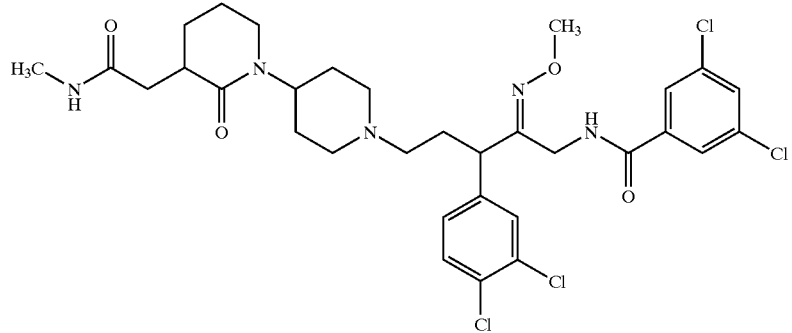
COMPOUND E
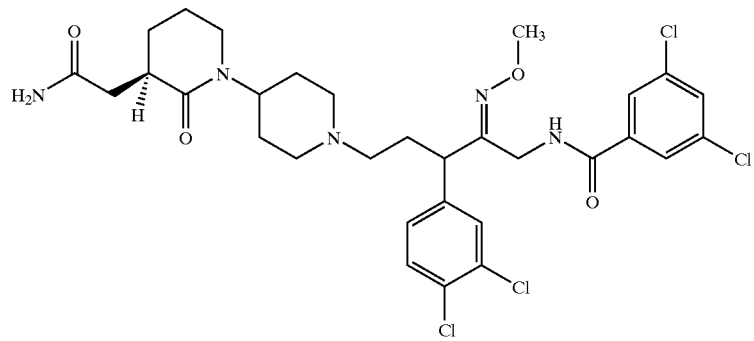

TABLE I-continued

COMPOUND F

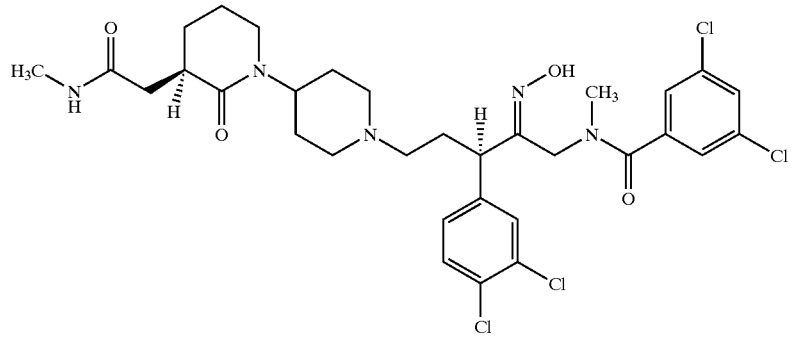

REPRODUCTIVE SYSTEM EFFECTS IN DOGS

Compound A was administered as an aqueous solution in sterile water by daily oral gavage to adult healthy beagle dogs.

The dogs received 28 consecutive daily doses at dose levels of 0, 15, 30 or 60 mg/kg. All dogs survived the treatment period. Compound A-related organ weight and histopathologic changes were observed in both males and females, in the testes, epididymides, prostate gland, ovaries, and uterus. Organ weights of male and female reproductive tract tissues were 33–86% lower than that of concurrent controls, and occurred in all dose groups. Microscopically, atrophy of seminiferous tubules (severe) in the testes, epididymides (minimal to moderate) and prostate gland (mild to moderate) was observed in all dose groups in males. Aspermia/hypospermia in the epididymides was also observed in all dose groups. In the epididymides, vacuolation (mild) of epithelium was also present in the mid- and high-dose males. In females, the ovaries and uteri from at least one dog in each dose group receiving Compound A appeared immature. This was characterized in the ovaries by a lack of antral follicles, and most follicles that were present were small and contained only small numbers of granulosa cells. Compared to control dogs, the uterine bodies and horns had less myometrial tissue present. Uterine epithelium from dogs receiving Compound A with immature uteri had very little cytoplasm present. The changes in the female reproductive system may be related to atrophy rather than immaturity.

To further characterize reproductive system effects, adult male healthy beagle dogs were administered sterile water (placebo) or Compound A orally by gavage for 1, 3 or 7 days (Day 0=first day of dosing). Serum was collected from blood for determination of serum concentrations of testosterone (T) and luteinizing hormone (LH).

Pretest and postdose control (placebo) serum LH and T concentrations typically had a pulsatile pattern with primarily lower baseline values interrupted by spikes of varying height and incidence. There were typically one to three spikes of LH and T within the sampling period. In many dogs the LH spikes preceded the T spikes by 20 to 40 minutes.

In dogs receiving Compound A, serum LH and T concentrations were generally near the lower baseline values at the first time point evaluated (1 hour after the first doses), and then typically declined throughout the 4-hour evaluation. This trend toward decreased LH and T concentrations from 60 to 300 minutes postdose was statistically significant ($p<0.0001$). LH and T remained at low concentrations for the remainder of the study. Compared to concurrent controls, group mean serum LH and T concentrations were significant lower at Day 0, 2 and 6 ($p \leq 0.0005$ for LH, $p \leq 0.0001$ for T). The decline in LH to very low (mean values of 1.5 to 3.8 ng/ml for Compound A versus 10.2 to 14.8 ng/ml for Controls) concentration was more rapid than that seen with T. In dogs receiving Compound A, serum LH and T concentrations at Day 2 were generally lower than those at Day 0. Serum LH concentrations on Day 6 were similar to those on Day 2, while serum T concentrations on Day 6 were generally lower than those on Day 2. By Days 2 and 6, some LH and many T samples were below the limit of detection despite using sensitive assays.

In addition to having overall low values of LH and T, dogs receiving Compound A lacked the normal pulsatile patterns of LH and T, although a few small pulses were occasionally observed.

Another study was conducted to evaluate the effects of lower doses (0.1, 0.5, 2.5, 12.5 mg/kg) of Compound A administered to male beagle dogs for 7 days. Histopathologic changes seen after dosing with Compound A included degeneration and cellular debris in the seminiferous tubules, interstitial cell vacuolation in the testes, epithelial vacuolation, atrophy, apoptosis, hypospermia, and interstitial edema of the epididymides. Epithelial apoptosis and atrophy of the prostate gland was also observed. Decreases in serum LH, T, DHEA (dehydroepiandrosterone), and androstenedione were clearly observed at doses of 2.5 and 12.5 mg/kg.

REVERSIBILITY OF THE EFFECTS ON HORMONES

The following investigative study was conducted to determine whether the changes observed after 1 week of Compound A administration were reversible after a 14-day postdose period. The first day of dosing was Day 1.

There were eight dogs in Group 1, who received placebo (sterile water) and twelve dogs in Group 2, who received Compound A. Dogs were scheduled to be dosed for 7 days; however, one dog died shortly after receiving the sixth dose of compound A. All eight dogs in Group 1 had hormonal evaluations on Day 7; 4 of these dogs were necropsied on Day 8. The remaining four dogs in Group 1 had hormonal evaluations on Day 21 (14 days postdose), and were necropsied on Day 22. In Group 2, eleven dogs had hormonal evaluations on Day 7, and five were necropsied on Day 8. The remaining six dogs in Group 2 had hormonal evaluations on Day 21 (14 days postdose) and were necropsied on Day 22.

Serum LH (luteinizing hormone) and T (testosterone) concentrations from pretest samples, and from control dogs from Days 7 and 21, often had a pulsatile pattern with primarily lower baseline values interrupted by spikes of varying height and incidence (although in some dogs the patterns were more erratic). There were typically one to three spikes of LH and T within the sampling period. In many dogs the LH spikes preceded the T spikes by 30 to 60 minutes. Androstenedione and DHEA concentrations tended to rise and fall with those of T, although in some dogs there were many values below the limit of quantitation.

In dogs receiving Compound A at Day 7, serum LH, T, androstenedione, and DHEA concentrations were often very low. Group mean values for LH, T, androstenedione, and DHEA were 14.7, 1.5, 0.37, and 0.88 ng/ml for dogs receiving sterile water, while dogs receiving Compound A had group mean values of 2.4, 0.05, 0.01 and 0.03 ng/ml, respectively. Compared to concurrent controls, group mean peak and peak mean serum LH, T, androstenedione, and DHEA concentrations were significantly lower at Day 7 ($p<0.001$ for LH, $p \leq 0.0043$ for T, $p \leq 0.001$ for androstenedione, and $p \leq 0.0002$ for DHEA). It should also be noted that on Day 7 almost all T, androstenedione, and DHEA samples were below the limit of detection despite using sensitive assays.

At Day 21, serum LH, T, androstenedione, and DHEA group mean and peak mean concentrations in dogs receiving Compound A were not significantly different from those of concurrent controls, indicating that the effects are reversible after a 14-day postdose period.

In summary, Compound A administration caused serum LH, T, androstenedione, and DHEA concentrations to decrease rapidly and dramatically, beginning shortly after a single dose. Because LH drives the release of androgens, including T, the changes in androgen levels may be due, in part, to the alterations in the level of LH. Moreover, it is also possible that a direct effect on androgen synthesis and/or release may be contributory to the changes observed.

REDUCTION OF SERUM TESTOSTERONE IN MICE

The effects of Compounds A, B, C, D, E and F on serum testosterone were tested in mice given intramuscular (i.m.) luteinizing hormone releasing hormone (LHRH) to drive testicular androgen biosynthesis.

Male nude mice (8 weeks old, 5 mice/group) were dosed orally with 0, 5, 15, 45, 90, 150 or 300 mg/kg of Compound A in 20% hydroxypropyl β-cyclodextran (HPβCD). After 1 hour, animals were given an i.m. injection of LHRH (250 ng/kg in 50 µl Sterile Water) into the biceps femoris muscle to drive testosterone production. After an additional hour, the animals were anesthetized with ketamine/xylazine, bled by cardiac puncture, and serum testosterone levels were determined by radioimmunoassay. Compound A reduced serum testosterone in a dose-dependent manner with 62% inhibition of serum testosterone at 15 mg/kg Compound A and a maximum of 83% inhibition at 300 mg/kg.

The effects of 90 mg/kg of Compounds A, B, C, D, E and F on LHRH-stimulated serum testosterone levels were compared in male nude mice. All compounds showed a statistically significant ($p<0.01$) reduction of serum testosterone except Compound D, which reduced mean serum testosterone by 19% but failed to reach statistical significance.

INHIBITION OF GROWTH OF ANDROGEN-DEPENDENT TUMORS IN MICE (SHIONOGI MURINE CARCINOMA)

Following the observation of reduction of serum testosterone in mice, the effects of Compound A on androgen-dependent tumor growth were tested. Two tumor models were used to determine whether Compound A could selectively inhibit growth of androgen-dependent tumors. Shionogi mouse mammary carcinoma tumors were grown in nude mice as an androgen-dependent model, and DU-145 human prostate carcinoma tumors were grown in nude mice as an androgen-independent model.

In the Shionogi experiment, male nu/nu mice (8–9 weeks old, 10 mice/group) were inoculated with Shionogi carcinoma cells and tumors were grown to approximately 150 mm$^3$ before initiation of Compound A administration. Mice were treated twice daily, i.p. with 20% HPβCD vehicle control, 5 mg/kg Compound A or 15 mg/kg Compound A. Tumor growth was inhibited over 15 days of Compound A treatment relative to vehicle control animals. At the end of 15 days, mean tumor volumes were inhibited by 41% and 69% in the 5 mg/kg and 15 mg/kg groups, respectively. These data indicate that Compound A can be used to treat or prevent growth of androgen-dependent tumors.

In the DU-145 experiment, male nu/nu mice (9–10 weeks old, 10 mice/group) were inoculated with DU-145 prostate carcinoma cells and tumors were grown to approximately 65 mm$^3$ before initiation of Compound A administration. Mice were treated twice daily, i.p. with 20% HPβCD vehicle control, 15 mg/kg, 45 mg/kg or 90 mg/kg of Compound A. As expected, tumor growth was not inhibited over 30 days in any of the Compound A groups. Castrated mice run in parallel also showed no inhibition of DU-145 tumor growth substantiating the androgen independence of this tumor model. Taken together with the Shionogi carcinoma results, these data indicate that Compound A is selective for androgen-dependent diseases, and lacks nonspecific effects on androgen-independent tumor growth.

What is claimed is:

1. A method of treating a symptom or disorder associated with a production and/or secretion of androgen comprising administering to a patient in need of such treatment a therapeutically effective amount of an antagonist selected from the group consisting of: (a) antagonists of neurokinin-1 ($NK_1$), neurokinin-2 ($NK_2$) and neurokinin-3 ($NK_3$) receptors, (b) antagonists of $NK_1$ and $NK_2$ receptors, (c) antagonists of $NK_2$ and $NK_3$ receptors, (d) antagonists of $NK_1$ and $NK_3$ receptors, (e) antagonists of $NK_1$ receptors, and (f) antagonists of $NK_2$ receptors.

2. The method of claim 1, wherein the antagonist administered to the patient is (a) the antagonist of $NK_1$, $NK_2$ and $NK_3$ receptors.

3. The method of claim 1, wherein the antagonist administered to the patient is (b) the antagonist of $NK_1$ and $NK_2$ receptors.

4. The method of claim 1, wherein the antagonist administered to the patient is (c) the antagonist of $NK_2$ and $NK_3$ receptors.

5. The method of claim 1, wherein the antagonist administered to the patient is (d) the antagonist of $NK_1$ and $NK_3$ receptors.

6. The method of claim 1, wherein the antagonist administered to the patient is (e) the antagonist of $NK_1$ receptors.

7. The method of claim 1, wherein the antagonist administered to the patient is (f) the antagonist of $NK_2$ receptors.

8. The method of claim 1 wherein the antagonist administered to the patient is a compound represented by the structural formula 1:

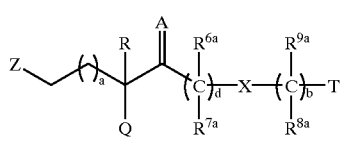

or a pharmaceutically acceptable salt thereof, wherein:
a is 0, 1, 2 or 3;
R is H, $C_{1-6}$ alkyl, —OH or $C_2$–$C_6$ hydroxyalkyl;
A is an optionally substituted oxime, optionally substituted hydrazone or optionally substituted olefin;
X is a bond, —C(O)—, —O—, —$NR^6$—, —S(O)$_e$—, —N($R^6$)C(O)—, —C(O)N($R^6$)— —OC(O)$NR^6$—, —OC(=S)$NR^6$—, —N($R^6$)C(=S)O—, —C(=NOR$^1$)—, —S(O)$_2$N($R^6$)—, —N($R^6$)S(O)$_2$—, —N($R^6$)C(O)O— or —OC(O)—;
b, d and e are each independently 0, 1 or 2;
T is H, phthalimidyl, aryl, heterocycloalkyl, heteroaryl, cycloalkyl or bridged cycloalkyl;
Q is —$SR^6$, —N($R^6$)($R^7$), —$OR^6$, phenyl, naphthyl or heteroaryl;
$R^{6a}$, $R^{7a}$, and $R^{8a}$ are each independently H, $C_{1-6}$ alkyl, $C_2$–$C_6$ hydroxyalkyl, $C_1$–$C_6$ alkoxy-$C_1$–$C_6$ alkyl, phenyl or benzyl;
$R^6$ and $R^7$ are each independently H, $C_{1-6}$ alkyl, $C_2$–$C_6$ hydroxyalkyl, $C_1$–$C_6$ alkoxy-$C_1$–$C_6$ alkyl, phenyl or benzyl; or $R^6$ and $R^7$, together with the nitrogen to which they are attached, form a ring;
$R^{9a}$ is $R^6$ or —$OR^6$;
Z is morpholinyl, optionally N-substituted piperazinyl, optionally substituted

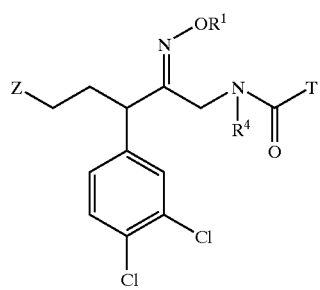

g is 0–3;
h is 1–4, provided the sum of h and g is 1–7;
wherein each aryl, heterocycloalkyl, heteroaryl, cycloalkyl and bridged cycloalkyl groups are all optionally substituted.

9. The method of claim 1 wherein the antagonist is a compound represented by the structural formula 2:

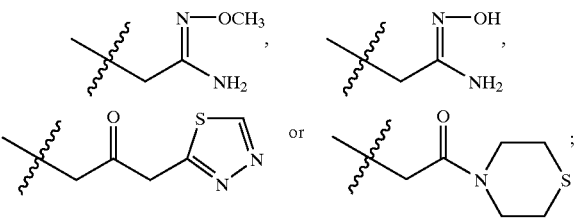

or a pharmaceutically acceptable salt thereof, wherein:
T is
1) phenyl, substituted with two or three substituents independently selected from the group consisting of:
   a) chloro;
   b) methyl, and
   c) methoxy; or
2) pyridyl, substituted with two or three substituents independently selected from the group consisting of:
   a) chloro, and
   b) methyl;
$R^1$ is H, methyl, ethyl, —$CH_2CN$, —$CH_2C(O)NH_2$, —$(CH_2)_3SO_3H$, —$CH_2C(O)NHCH_3$, —$CH_2C(O)NHOH$, —$CH_2C(O)NHOCH_3$, —$CH_2C(O)NHCH_2CN$, —$CH_2F$, —$CH_2C(O)NHCH_2SO_3H$,

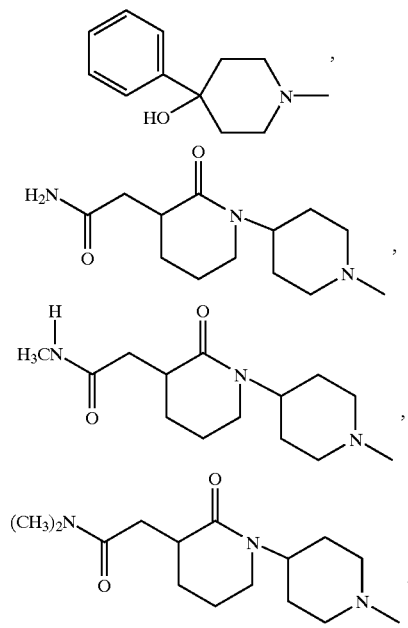

$R^4$ is methyl or ethyl; and
Z is

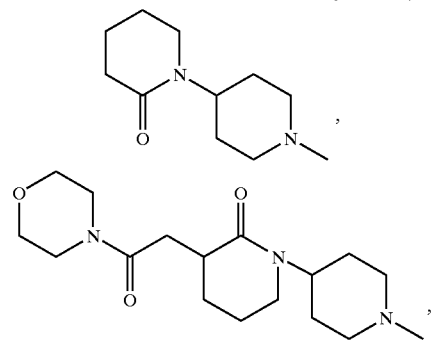

-continued
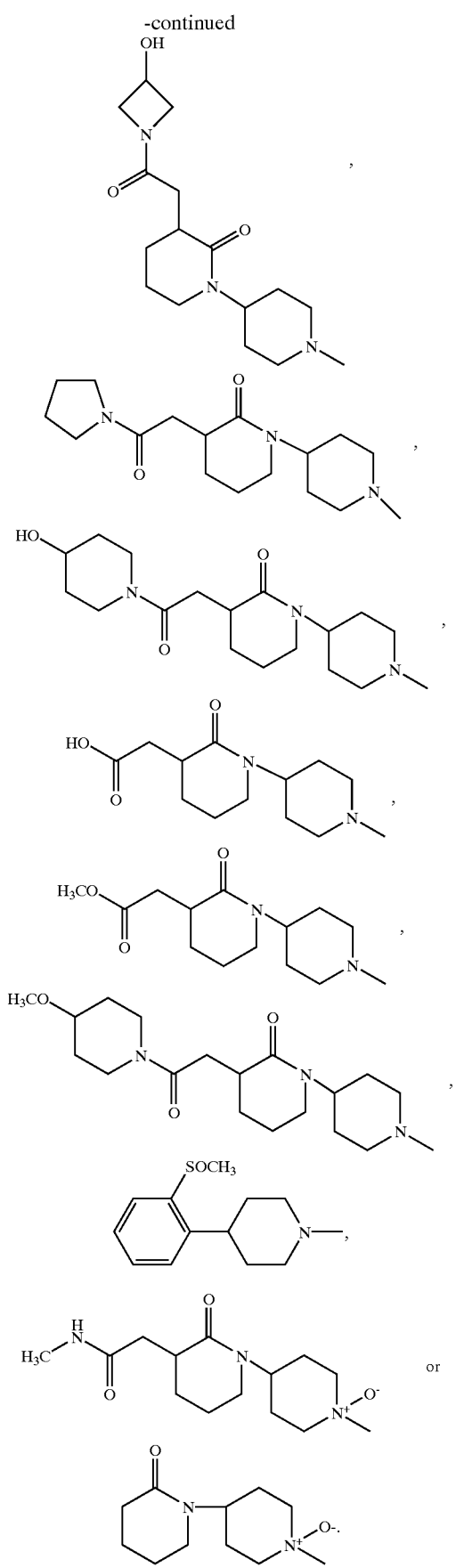
10. The method of claim 9 wherein, for the compound,
T is phenyl, substituted with two or three substituents independently selected from the group consisting of:
a) chloro;
b) methyl, and
c) methoxy;
$R^1$ is H, methyl, —$CH_2F$, —$CH_2CN$, —$(CH_2)_3SO_3H$,
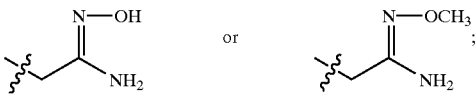
$R^4$ is methyl, and
Z is
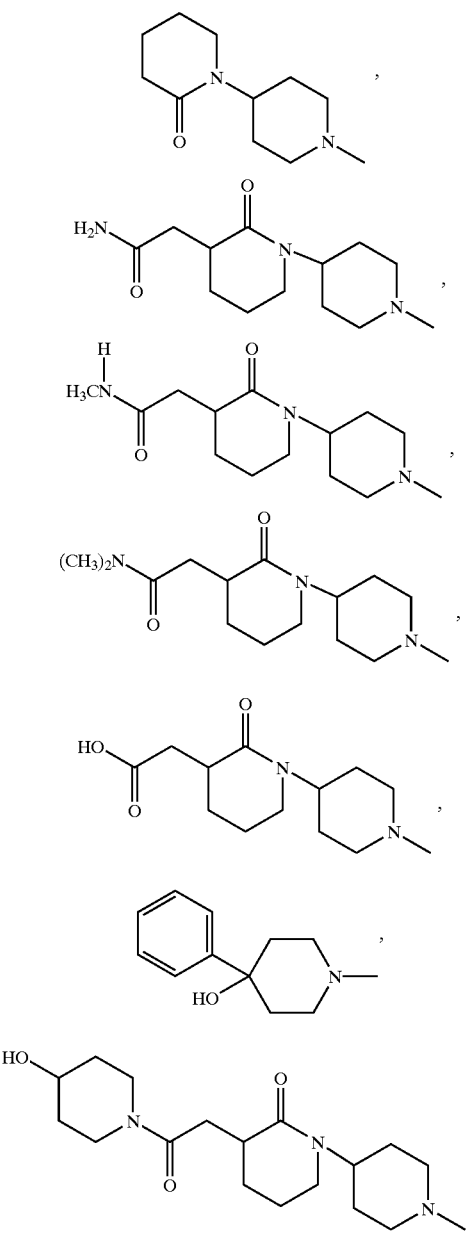

-continued
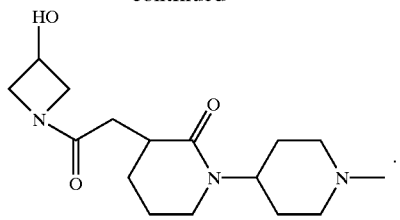
11. The method of claim 9 wherein, for the compound,
T is phenyl, substituted with 2 chloro substituents;
R$^1$ is H or methyl;
R$^4$ is methyl, and
Z is
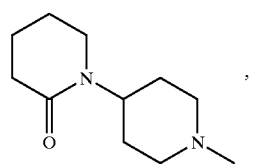
-continued
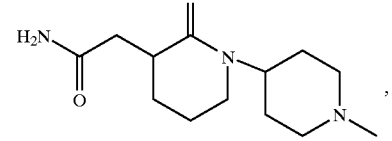
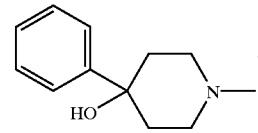
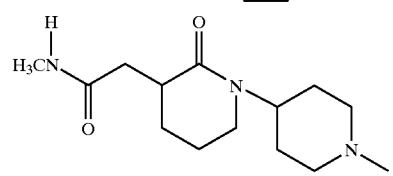
or
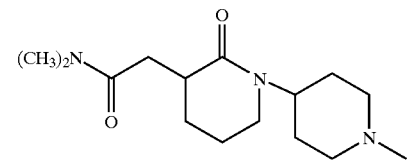
12. The method of claim 1 wherein the antagonist is selected from the group consisting of:
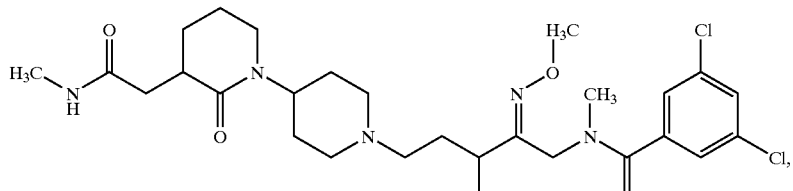
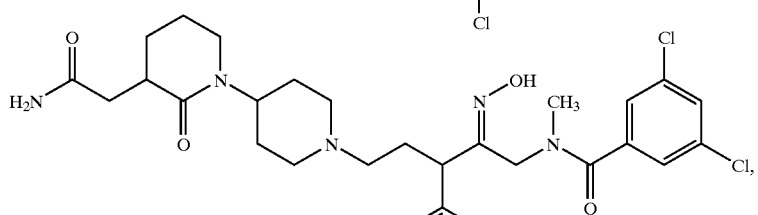
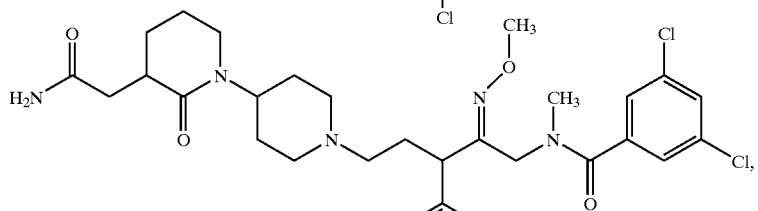

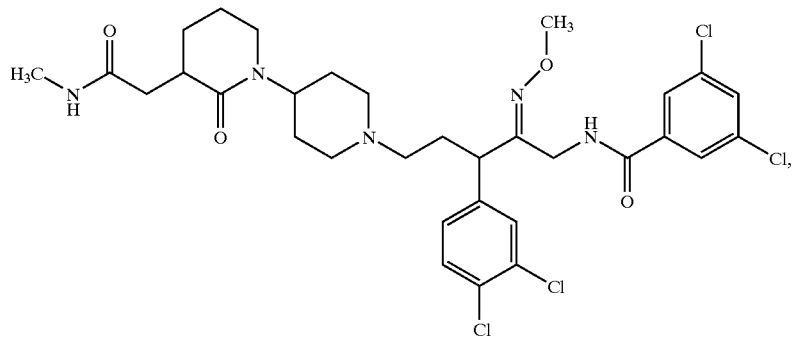

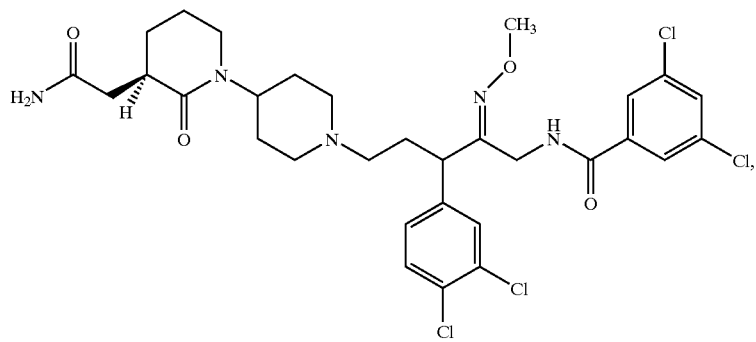

and

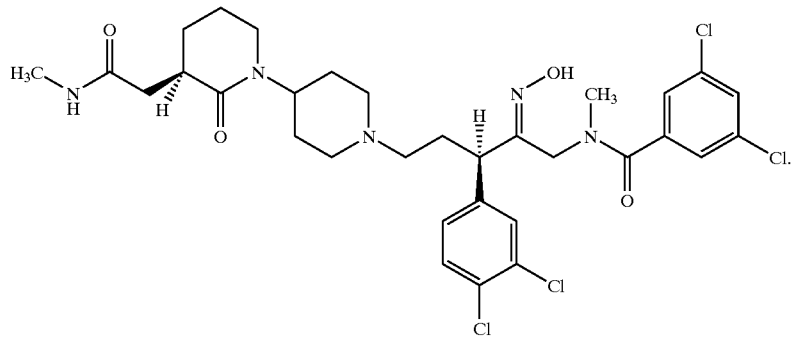

13. The method of claim 1 wherein the symptom or disorder is associated with an overproduction of androgen or excessive androgen stimulation.

14. The method of claim 1 wherein the symptom or disorder is selected from the group consisting of benign prostatic hyperplasia, metastatic carcinoma, testicular cancer, androgen dependent acne, male pattern baldness, precocious puberty in boys, hyperandrogenism, hirsutism, virilization, PCOS, HAIR-AN syndrome, ovarian hyperthecosis, follicular maturation arrest, artesia, anovulation, dysmenorrhea, dysfunctional uterine bleeding, infertility, and androgen-producing tumors.

15. A method of treating a symptom or disorder associated with a production and/or secretion of androgen comprising administering to a patient in need of such treatment a therapeutically effective amount of a pharmaceutical composition comprising a pharmaceutically acceptable carrier and an antagonist selected from the group consisting of: (a) antagonists of neurokinin-1 ($NK_1$), neurokinin-2 ($NK_2$) and neurokinin-3 ($NK_3$) receptors, (b) antagonists of $NK_1$ and $NK_2$ receptors, (c) antagonists of $NK_2$ and $NK_3$ receptors, (d) antagonists of $NK_1$ and $NK_3$ receptors, (e) antagonists of $NK_1$ receptors, and (f) antagonists of $NK_2$ receptors.

16. A method of treating a symptom or disorder associated with a production and/or secretion of androgen comprising administering to a patient in need of such treatment a therapeutically effective amount of a pharmaceutical composition comprising the antagonist of formula 1 as defined in the method of claim 8 and a pharmaceutically acceptable carrier.

17. A method of treating a symptom or disorder associated with a production and/or secretion of androgen comprising administering to a patient in need of such treatment a therapeutically effective amount of a pharmaceutical composition comprising a pharmaceutically acceptable carrier and an antagonist selected from the group consisting of:

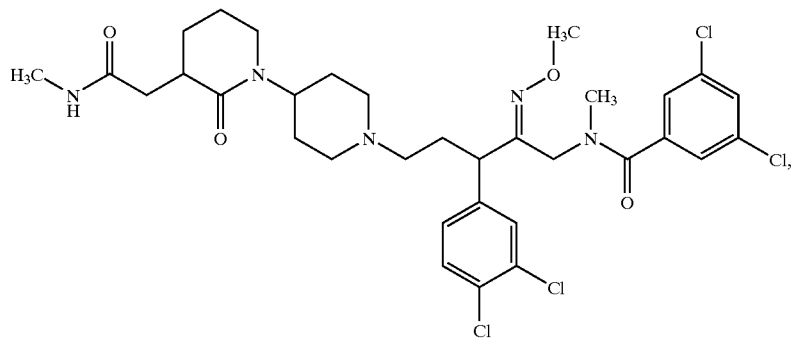
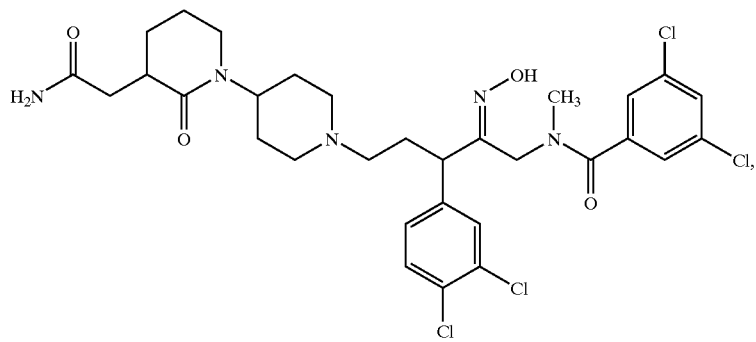
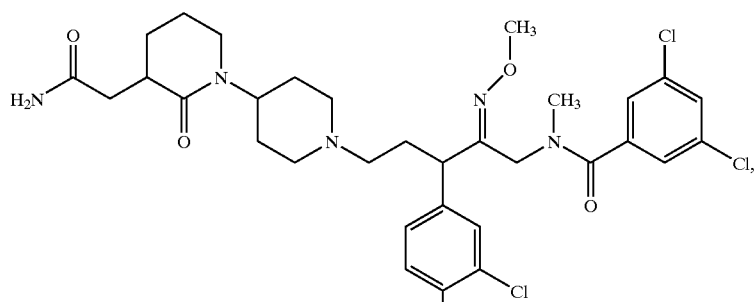
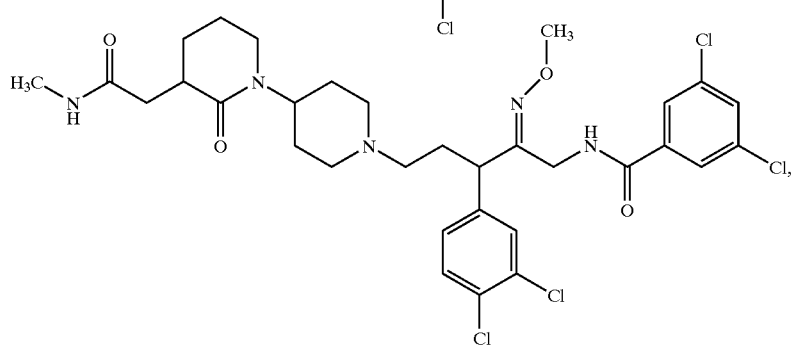
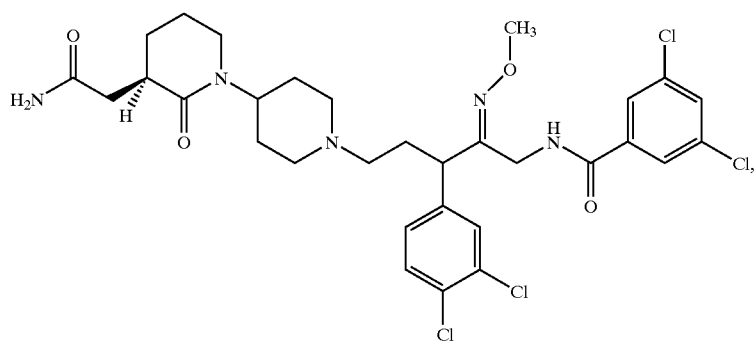
and

-continued

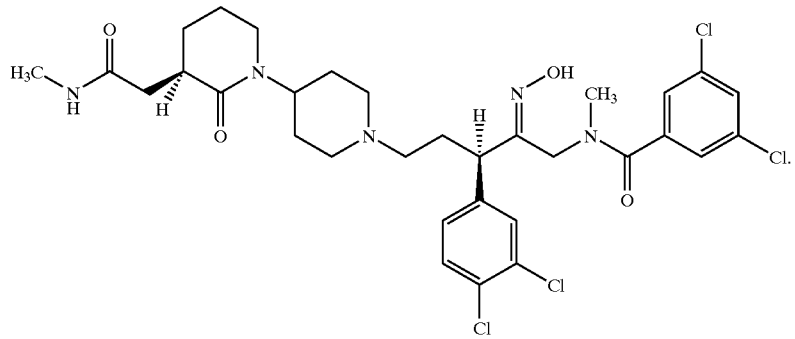

18. The method of claim 15, wherein the symptom or disorder is selected from the group consisting of benign prostatic hyperplasia, metastatic carcinoma, testicular cancer, androgen dependent acne, male pattern baldness, precocious puberty in boys, hyperandrogenism, hirsutism, virilization, PCOS, HAIR-AN syndrome, ovarian hyperthecosis, follicular maturation arrest, atresia, anovulation, dysmenorrhea, dysfunctional uterine bleeding, infertility, and androgen-producing tumors.

19. The method of claim 16, wherein the symptom or disorder is selected from the group consisting of benign prostatic hyperplasia, metastatic carcinoma, testicular cancer, androgen dependent acne, male pattern baldness, precocious puberty in boys, hyperandrogenism, hirsutism, virilization, PCOS, HAIR-AN syndrome, ovarian hyperthecosis, follicular maturation arrest, atresia, anovulation, dysmenorrhea, dysfunctional uterine bleeding, infertility, and androgen-producing tumors.

20. The method of claim 17, wherein the symptom or disorder is selected from the group consisting of benign prostatic hyperplasia, metastatic carcinoma, testicular cancer, androgen dependent acne, male pattern baldness, precocious puberty in boys, hyperandrogenism, hirsutism, virilization, PCOS, HAIR-AN syndrome, ovarian hyperthecosis, follicular maturation arrest, atresia, anovulation, dysmenorrhea, dysfunctional uterine bleeding, infertility, and androgen-producing tumors.

21. A method of treating a symptom or disorder associated with a production and/or secretion of luteinizing hormone (LH) comprising administering to a patient in need of such treatment a therapeutically effective amount of an antagonist selected from the group consisting of: (a) antagonists of neurokinin-1 ($NK_1$), neurokinin-2 ($NK_2$) and neurokinin-3 ($NK_3$) receptors, (b) antagonists of $NK_1$ and $NK_2$ receptors, (c) antagonists of $NK_2$ and $NK_3$ receptors, (d) antagonists of $NK_1$ and $NK_3$ receptors, (e) antagonists of $NK_1$ receptors, and (f) antagonists of $NK_2$ receptors.

22. A method of treating a symptom or disorder selected from the group consisting of benign prostatic hyperplasia, metastatic carcinoma, testicular cancer, androgen dependent acne, male pattern baldness, precocious puberty in boys, hyperandrogenism, hirsutism, virilization, PCOS, HAIR-AN syndrome, ovarian hyperthecosis, follicular maturation arrest, atresia, anovulation, dysmenorrhea, dysfunctional uterine bleeding, infertility, and androgen-producing tumors, by modulating a production and/or secretion of androgen and/or luteinizing hormone, comprising administering to a patient in need of such treatment a therapeutically effective amount of an antagonist selected from the group consisting of: (a) antagonists of neurokinin-1 ($NK_1$), neurokinin-2 ($NK_2$) and neurokinin-3 ($NK_3$) receptors, (b) antagonists of $NK_1$ and $NK_2$ receptors, (c) antagonists of $NK_2$ and $NK_3$ receptors, (d) antagonists of $NK_1$ and $NK_3$ receptors, (e) antagonists of $NK_1$ receptors, and (f) antagonists of $NK_2$ receptors.

23. A method of inhibiting a production and/or secretion of an androgen in a mammal, comprising administering to the mammal an inhibitory amount of the compound of formula 1 as defined in the method of claim 8.

24. A method of inhibiting a production and/or secretion of an androgen in a mammal, comprising administering to the mammal an inhibitory amount of the compound of formula 2 as defined in the method of claim 9.

25. A method of inhibiting a production and/or secretion of luteinizing hormone (LH) in a mammal, comprising administering to the mammal an inhibitory amount of the compound of formula 1 as defined in the method of claim 8.

26. A method of inhibiting a production and/or secretion of luteinizing hormone (LH) in a mammal, comprising administering to the mammal an inhibitory amount of the compound of formula 2 as defined in the method of claim 9.

27. A method of modulating the level of an androgen in a mammal, comprising administering to the mammal an effective amount of the compound of formula 1 as defined in the method of claim 8.

28. A method of modulating the level of an androgen in a mammal, comprising administering to the mammal an effective amount of the compound of formula 2 as defined in the method of claim 9.

29. A method of modulating the level of luteinizing hormone in a mammal, comprising administering to the mammal an effective amount of the compound of formula 1 as defined in the method of claim 8.

30. A method of modulating the level of luteinizing hormone in a mammal, comprising administering to the mammal an effective amount of the compound of formula 2 as defined in the method of claim 9.

* * * * *